(12) United States Patent
Fukuda et al.

(10) Patent No.: US 10,398,442 B2
(45) Date of Patent: Sep. 3, 2019

(54) STENT

(71) Applicant: MEIJO UNIVERSITY, Nagoya-shi, Aichi (JP)

(72) Inventors: Toshio Fukuda, Nagoya (JP); Akihiko Ichikawa, Nagoya (JP); Takahiro Ito, Nagoya (JP)

(73) Assignee: MEIJO UNIVERSITY, Nagoya-shi, Aichi (JP)

( * ) Notice: Subject to any disclaimer, the term of this patent is extended or adjusted under 35 U.S.C. 154(b) by 61 days.

(21) Appl. No.: 15/306,865

(22) PCT Filed: May 13, 2015

(86) PCT No.: PCT/JP2015/063745
§ 371 (c)(1),
(2) Date: Oct. 26, 2016

(87) PCT Pub. No.: WO2015/178266
PCT Pub. Date: Nov. 26, 2015

(65) Prior Publication Data
US 2017/0049456 A1  Feb. 23, 2017

(30) Foreign Application Priority Data
May 19, 2014 (JP) .................................. 2014-103330

(51) Int. Cl.
*A61F 2/90* (2013.01)
*A61B 17/00* (2006.01)
(Continued)

(52) U.S. Cl.
CPC .. *A61B 17/12118* (2013.01); *A61B 17/00491* (2013.01); *A61B 17/1214* (2013.01);
(Continued)

(58) Field of Classification Search
CPC .................................................. A61F 2002/823
See application file for complete search history.

(56) References Cited

U.S. PATENT DOCUMENTS 6,261,257 B1 * 7/2001 Uflacker ............. A61M 1/3655
604/175
6,610,031 B1 * 8/2003 Chin .................. A61M 39/045
604/167.04
(Continued)

FOREIGN PATENT DOCUMENTS

JP    2001-238964 A    9/2001
JP    2003-250907 A    9/2003
(Continued)

OTHER PUBLICATIONS

Written Opinion of the International Searching Authority dated Jul. 17, 2015 for PCT/JP2015/06375 (7 pages).
(Continued)

*Primary Examiner* — Jacqueline Woznicki
(74) *Attorney, Agent, or Firm* — Smith, Gambrell & Russell, LLP

(57) ABSTRACT

Providing a stent which can easily be indwelled in a blood vessel in a state such that a catheter can be projected toward an inside of aneurysm. The stent is a stent for use in medical treatment of an aneurysm (1) and includes a cylindrical stent body (10) provided on a peripheral wall and having a plurality of insertion portions (11) through each of which a catheter (7) is insertable and a plurality of valving elements (20) provided in the insertion portions (11) respectively. Each valving element (20) is opened when the catheter (7) is inserted through one of the insertion portions (11). Each valving element (20) is closed when the catheter (7) is pulled out of the insertion portion (11). This suppresses an outflow into a blood vessel of a coil (9) placed in the aneurysm (1).

15 Claims, 4 Drawing Sheets

(51) Int. Cl.
*A61M 39/04* (2006.01)
*A61F 2/06* (2013.01)
*A61B 17/12* (2006.01)
*A61F 2/24* (2006.01)
*A61F 2/82* (2013.01)

(52) U.S. Cl.
CPC .......... *A61B 17/12172* (2013.01); *A61F 2/90* (2013.01); *A61B 2017/00495* (2013.01); *A61B 2017/00522* (2013.01); *A61B 2017/1205* (2013.01); *A61F 2/2418* (2013.01); *A61F 2002/061* (2013.01); *A61F 2002/823* (2013.01); *A61F 2230/0023* (2013.01); *A61F 2250/0018* (2013.01); *A61F 2250/0029* (2013.01); *A61M 39/04* (2013.01)

(56) References Cited

U.S. PATENT DOCUMENTS

| | | | | |
|---|---|---|---|---|
| 2001/0012960 | A1* | 8/2001 | Acciai | A61F 2/90 623/1.15 |
| 2001/0037808 | A1* | 11/2001 | Deem | A61B 17/12022 128/200.24 |
| 2003/0018294 | A1* | 1/2003 | Cox | A61B 17/12022 604/20 |
| 2003/0109917 | A1 | 6/2003 | Rudin et al. | |
| 2004/0199246 | A1* | 10/2004 | Chu | A61F 2/90 623/1.32 |
| 2009/0157014 | A1* | 6/2009 | Osborne | A61M 39/0208 604/264 |
| 2010/0106240 | A1* | 4/2010 | Duggal | A61B 17/12022 623/1.15 |
| 2011/0022149 | A1* | 1/2011 | Cox | A61B 17/12118 623/1.11 |
| 2011/0160833 | A1* | 6/2011 | Gonzalez | A61F 2/07 623/1.11 |
| 2011/0270373 | A1 | 11/2011 | Sampognaro et al. | |
| 2013/0218255 | A1* | 8/2013 | Cattaneo | A61B 17/12118 623/1.11 |
| 2013/0325103 | A1* | 12/2013 | Arai | A61F 2/2418 623/1.24 |

FOREIGN PATENT DOCUMENTS

| | | |
|---|---|---|
| JP | 2003-265620 A | 9/2003 |
| JP | 2005-503201 A | 2/2005 |
| JP | 2013-509912 A | 3/2013 |
| JP | 2015-036107 A | 2/2015 |

OTHER PUBLICATIONS

International Preliminary Report on Patentability of the International Searching Authority dated Nov. 22, 2016 for PCT/JP2015/06375 (9 pages).
International Search Report for PCT/JP2015/063745, dated Aug. 4, 2015 in English & Japanese Language.

* cited by examiner

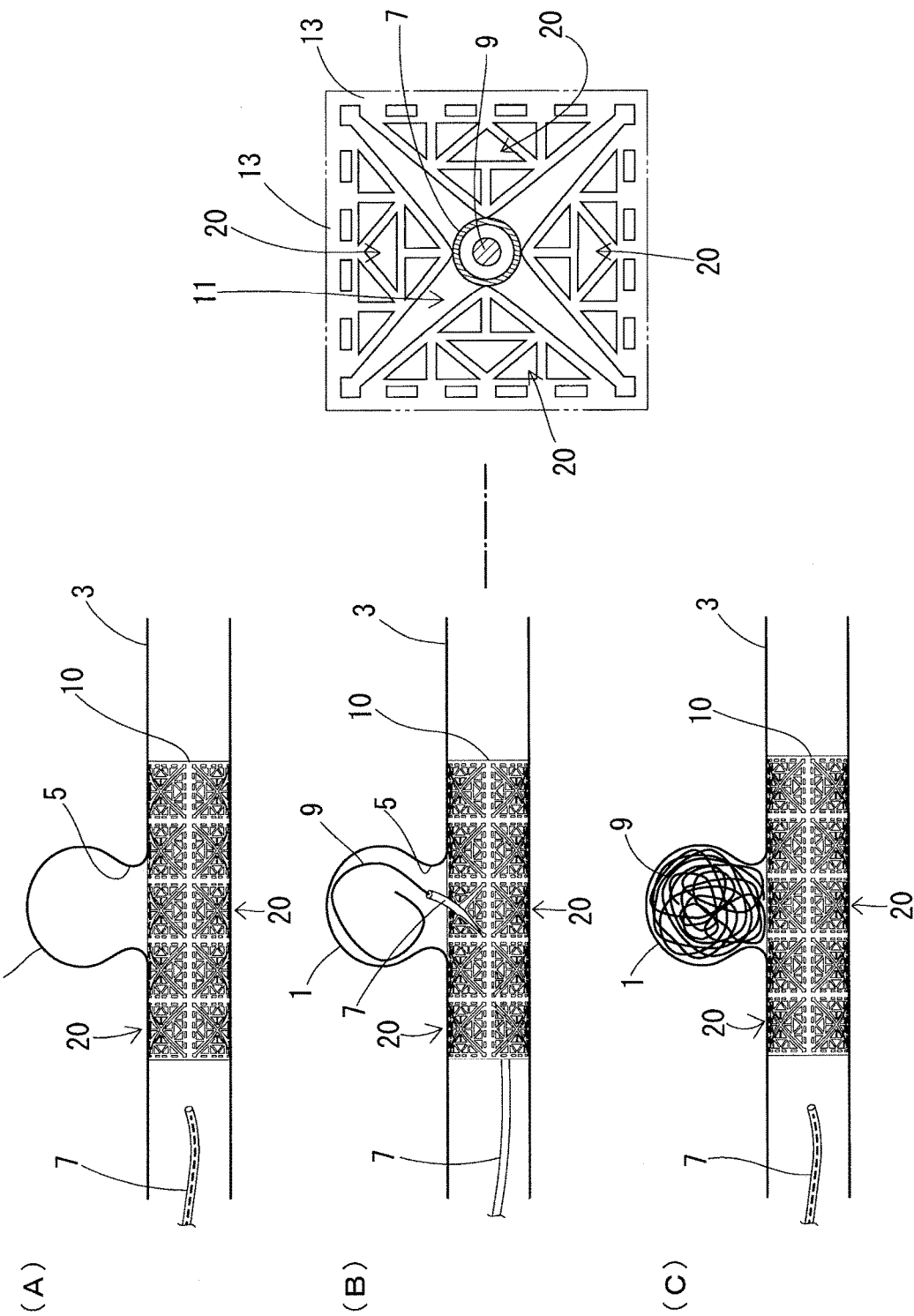

STENT

TECHNICAL FIELD

The present invention relates to a stent.

BACKGROUND ART

Patent Document 1 discloses a conventional stent. This stent includes a stent body and a valving element and is cylindrical in shape. The stent body is formed into a mesh pattern and has one insertion hole through which a catheter is insertable. The valving element is provided to cover the insertion hole of the stent body. The valving element has a flange-shaped base bonded to an outer peripheral edge of the insertion hole of the stent body and a projection which projects outside the stent body from the base. The projection comprises an elastic membrane and has a top formed with a linear shaped slit.

This stent is indwelled in a blood vessel so that the valving element is located in proximity to an opening of an aneurysm and so that the projection projects toward an inside of the aneurysm. A distal end of the catheter expands the slit from inside, projecting to place an embolic material into the aneurysm. Subsequently, when the catheter is pulled out, the slit is closed to adhere tightly. As a result, this stent can suppress outflow into the blood vessel of the embolic material placed in the aneurysm.

PRIOR ART DOCUMENT

Patent Documents

Patent Document 1: Japanese Patent Application Publication No. JP-A-2003-250907

SUMMARY OF THE INVENTION

Problem to be Overcome by the Invention

However, the stent of Patent Document 1 has a single insertion hole through which the catheter is inserted and needs to be indwelled in the blood vessel so that the projection of the valving element provided in the insertion hole projects toward the inside of the aneurysm. A high-level technique is required in order that the stent may be located at a proper position in the blood vessel.

The present invention was made in view of the above-described circumstances in the conventional art and provides a stent which can easily be indwelled in the blood vessel so that the catheter can be projected toward the inside of the aneurysm.

Means for Overcoming the Problem

A stent of the present invention is for use in medical treatment of aneurysm, includes a cylindrical stent body provided on a peripheral wall and having a plurality of insertion portions through each of which a catheter is insertable and a plurality of valving elements provided in the insertion portions respectively, each valving element being opened when the catheter is inserted through one of the insertion portions, each valving element being closed when the catheter is pulled out of the insertion portion, so that outflow into the blood vessel of an embolic material placed in the aneurysm is suppressed.

This stent is provided with the plurality of insertion portions on the peripheral wall of the stent body and the valving elements in the respective insertion portions. Accordingly, when the stent is indwelled in the blood vessel so as to sufficiently cover an opening of the aneurysm, one of the insertion portions can be selected which can open toward the opening of the aneurysm from the plural insertion portions, and the catheter can be projected toward the inside of the aneurysm while the valving element is open. Furthermore, although the plural insertion portions are provided in the peripheral wall of the stent body, the insertion portions except for the insertion portion through which the catheter has been inserted are closed by the respective valving elements. Furthermore, the insertion portion through which the catheter has been inserted is also closed by the valving element when the catheter is pulled out after the embolic material has been placed in the aneurysm and the aneurysm has been obturated. As a result, the stent can suppress an outflow into the blood vessel of the embolic material placed in the aneurysm.

Accordingly, the stent according to the present invention can easily be indwelled in the blood vessel in a state such that the catheter can be projected toward the inside of the aneurysm.

BRIEF DESCRIPTION OF THE DRAWINGS

FIG. 4 illustrates an aneurysm embolization using the stent of the first embodiment, showing (A) the state where the stent is indwelled, (B) the state where a coil is placed into the aneurysm and (C) the state where the aneurysm is obturated by the coil.

BEST MODE FOR CARRYING OUT THE INVENTION

Favorable forms of the present invention will be described.

In the stent of the present invention, each valving element may be formed into a mesh pattern. In this case, since the stent indwelled in the blood vessel is early covered with cells of the blood vessel wall after medical treatment, formation of blood clot can be suppressed in an early stage.

In the stent of the present invention, each valving element is made of a material that is identical with a material of the stent body and is formed integrally with the stent body. In this case, since the stent body and the valving elements are integrally made of the same material, the valving elements are prevented from separation from the stent body. Further, the time and effort to mount the valving elements to the stent body can be avoided.

The stent of the present invention may have an outer periphery without any asperity. In this case, the stent is less likely to damage a blood vessel wall since the stent has no asperity on the outer periphery. Furthermore, since the stent is indwelled in the blood vessel with the outer periphery in contact with the blood vessel wall, the stent is early covered with cells of the blood vessel wall after the medical treatment and formation of blood clot can be suppressed in an early stage.

In the stent of the present invention, each valving element may be formed into a triangular mesh pattern. In this case, when boundaries between the stent body formed with the insertion portions and the valving elements are formed into a linear shape and each boundary serves as one of sides of triangle, triangular valving elements can be formed so that one of apexes away from each boundary is located at a central part of each insertion portion. As a result, the catheter can be inserted through the insertion portion while one side of the valving element formed on the boundary is bent.

In the stent of the present invention, the valving elements may be formed into a plurality of types of similar mesh patterns differing in size and each valving element may have a fractal structure. In this case, when the valving elements each having the fractal structure are closed, resistance against flow of blood flowing from the blood vessel into the aneurysm is increased, so that an amount of blood flowing into the aneurysm can be suppressed.

Next, a first embodiment of the stent of the present invention will be described with reference to the accompanying drawings.

First Embodiment

Figure 1:
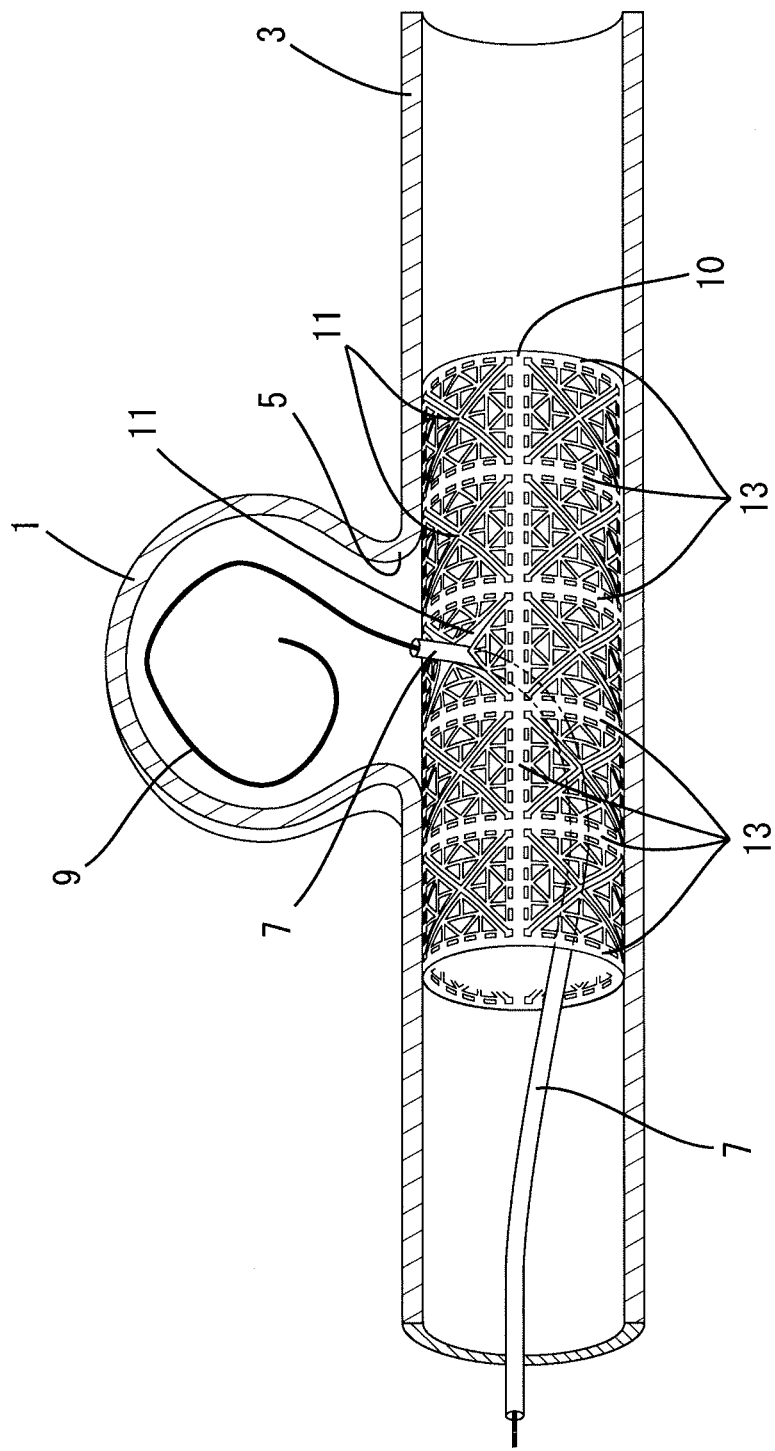
FIG. 1 is a schematic view showing the state where a stent of a first embodiment is indwelled in a blood vessel and a coil is placed into an aneurysm.

A stent of the first embodiment is cylindrical in shape and is used for medical treatment for an aneurysm 1, as shown in FIG. 1. More specifically, this stent is used for an aneurysm embolization in which the stent is indwelled in a blood vessel 3 so as to sufficiently cover an opening 5 of the aneurysm 1 and in which a coil 9 made of stainless steel, serving as an embolic material, is placed into the aneurysm 1 from a catheter 7 inserted through one of insertion portions 11 in order to obturate the aneurysm 1, which insertion portions 11 will be described later.

Figure 2:
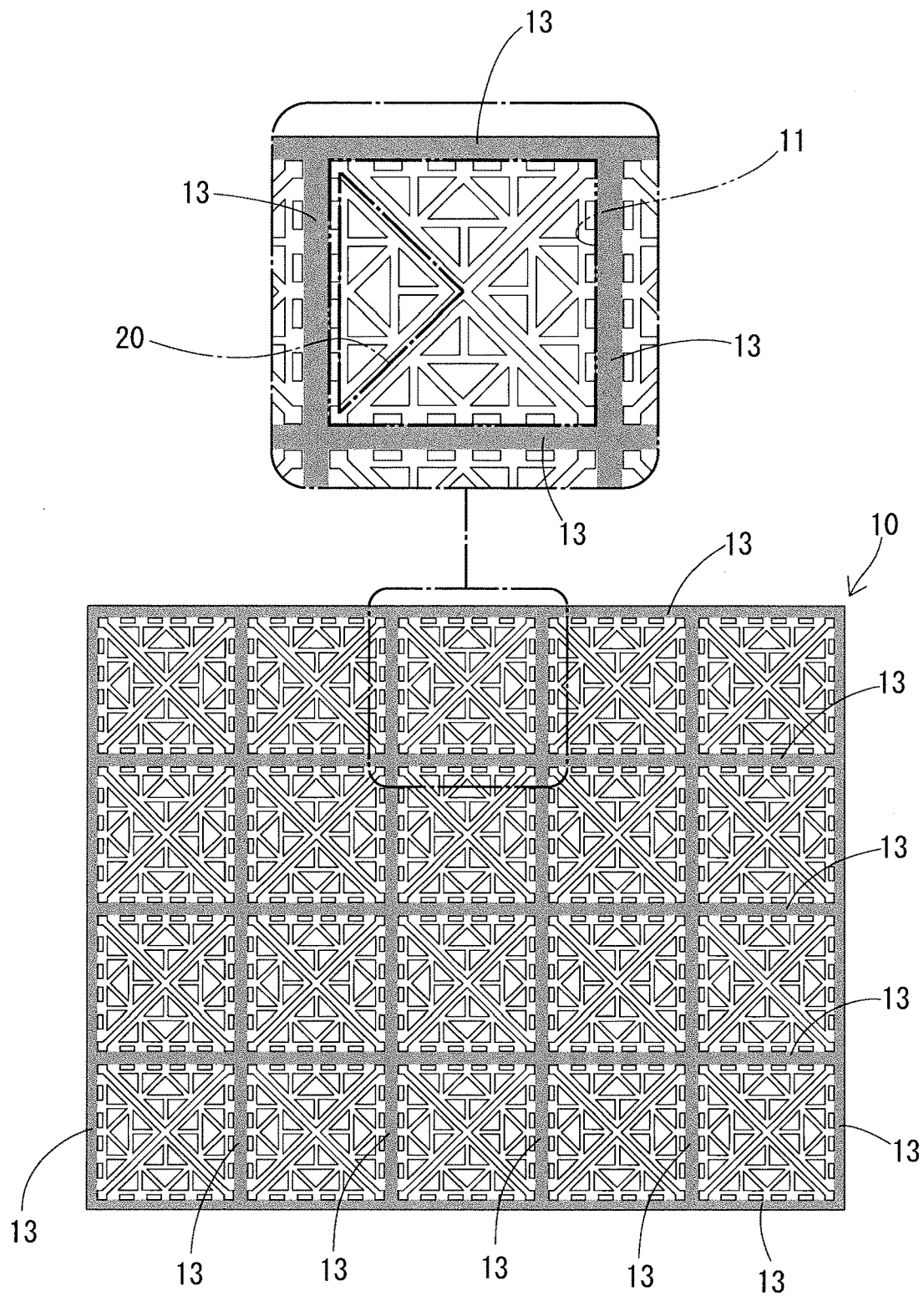
FIG. 2 is a development view of the stent of the first embodiment and a partially enlarged view of the stent.

This stent includes a cylindrical stent body 10 having a plurality of the insertion portions 11 through which the catheter 7 can be inserted and valving elements 20 provided in the insertion portions 11 respectively, as shown in FIGS. 1 and 2. The stent body 10 and the valving elements 20 are formed integrally of the same material. The stent is made of an alloy and has elasticity.

The stent body 10 is composed of connecting bands 13 (grayed portions in FIG. 2) extending linearly at regular intervals in a longitudinal direction (a circumferential direction with respect to the cylindrical shape) and in a lateral direction (an axial direction with respect to the cylindrical shape), as shown in a developed view of FIG. 2. The stent body 10 is provided with four square insertion portions 11 surrounded respectively by the connecting bands 13 and arranged continuously in the longitudinal direction (a circumferential direction with respect to the cylindrical shape) and five square insertion portions 11 in the lateral direction (the axial direction with respect to the cylindrical direction). Each insertion portion 11 has a size such that the catheter 7 can be inserted therethrough.

Figure 3:
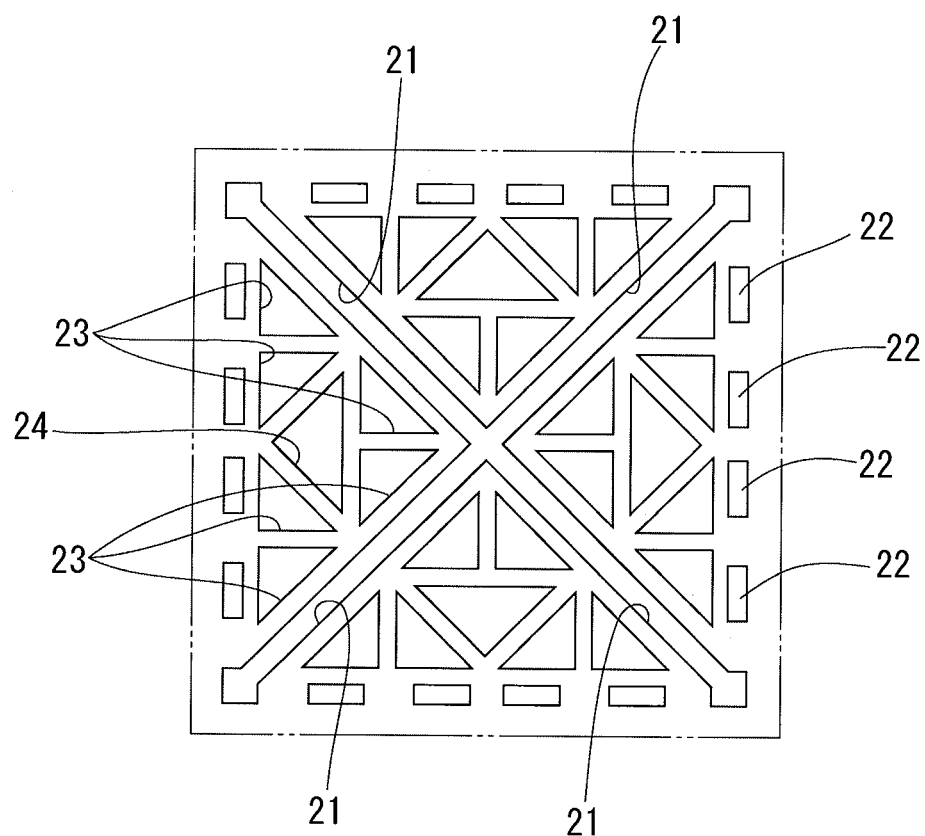
FIG. 3 is an enlarged view of a single insertion portion and a valving element of the stent of the first embodiment.

The valving elements 20 provided in the respective insertion portions 11 are formed, as shown in FIGS. 2 and 3, into an isosceles triangle extending inward from respective sides of the square insertion portions 11 and having one sides which are sides of the insertion portions 11, and having apexes located in central parts of the insertion portions 11 respectively. Four valving elements 20 are provided for every one of the insertion portions 11. Each valving element 20 provided in each insertion portion has two oblique sides extending from the apex thereof. Interstices 21 are formed between the oblique sides of each valving element 20 and the oblique sides of adjacent valving elements respectively. As a result, each insertion portion 11 is formed with an X-shaped interstice 21 along diagonal lines. Each interstice 21 is formed to be narrow so that no large opening is formed in each insertion portion 11.

Each valving element 20 is formed into a mesh pattern including four rectangular openings 22 arranged along respective sides of each insertion portion 11 and seven openings 23 and 24 formed by two types of sizes of similar isosceles triangles. More specifically, each valving element 20 has a fractal structure formed into a plurality of types of similar mesh patterns with different sizes.

Thus, this stent has a linear boundary between the connecting band 13 of the stent body 10 forming each insertion portion 11 and each valving element 20. Accordingly, as shown in FIGS. 1 and 4(B), when part of each valving element 20 is pushed outward by a distal end of the catheter 7 from an inside of the stent, each valving element 20 is curved while one side of each valving element 20 formed at the boundary is bent, whereby the insertion portion 11 is opened with the result that the catheter 7 can be inserted through the insertion portion 11. Furthermore, the stent body 10 and the valving elements 20 are made of an alloy and accordingly have elasticity. As a result, when the catheter 7 is pulled out of the insertion portion 11, the valving element 20 is returned by an elastic force to the position along an outer periphery of the cylindrical stent body 10, thereby closing the insertion portion 11.

Furthermore, each valving element 20 is formed into the isosceles triangle having a side of the square insertion portion 11 as one of sides thereof and an apex located in the central part of the insertion portion 11. The valving elements 20 are formed into the mesh-patterned fractal structure by the similar isosceles triangular openings 23 and 24 having two types of sizes respectively. As a result, since the valving elements 20 have a predetermined strength and can retain the elastic force, the valving elements 20 can be returned to the respective positions along the outer periphery of the cylindrical stent body 10, so that the insertion portions 11 can reliably be closed.

Furthermore, since the stent body 10 and the valving elements 20 are integrally made of the same material, the valving elements 20 are prevented from separation from the stent body 10. Further, no work is required for the attachment of the valving elements 20 to the stent body 10. Further, the stent has no asperity on the outer periphery formed by the cylindrical stent body 10 and the valving elements 20.

The aneurysm embolization with use of thus configured stent will now be described.

Firstly, as shown in FIG. 4(A), the stent is indwelled in the blood vessel 3 so as to sufficiently cover the opening 5 of the aneurysm 1. In this case, the stent is less likely to damage a blood vessel wall since the stent has no asperity on the outer periphery.

Subsequently, as shown in FIG. 4(B), one of the insertion portions 11 which can be opened toward the opening 5 of the aneurysm 1 is selected. The valving element 20 provided in the selected insertion portion 11 is pushed by a distal end of the catheter 7 to be expanded, and the distal end of the catheter 7 is caused to project toward the inside of the aneurysm 1 while the valving element 20 is opened. Since a plurality of insertion portions 11 is continuously provided on a peripheral wall of the stent body 10, there is less necessity to take into account the orientation of the insertion portion 11 through which the catheter 7 is inserted when indwelling the stent in the blood vessel 3. More specifically, one of a plurality of insertion portions 11 can be selected which can be opened toward the opening 5 of the aneurysm 1 and the distal end of the catheter 7 can be projected toward the inside of the aneurysm.

Accordingly, the stent of the first embodiment can easily be indwelled in the blood vessel 3 in a state such that the catheter 7 can be projected toward the inside of the aneurysm 1.

The coil 9 is placed from the distal end opening of the catheter 7 into the inside of the aneurysm 1 thereby to obturate the aneurysm 1, as shown in FIG. 4(C). Subsequently, the catheter 7 is pulled out of the insertion portion 11. The elastic force returns the valving element 20 to the position along the outer periphery of the cylindrical stent body 10, closing the valving element 20. The aneurysm embolization with use of the stent is finished in this manner.

Thus, although a plurality of insertion portions 11 is provided on the peripheral wall of the stent body 10, the insertion portions 11 except for the insertion portion 11 through which the catheter 7 has been inserted are closed by the respective valving elements 20. Furthermore, the insertion portion 11 through which the catheter 7 has been inserted is also closed by the valving element 20 when the catheter 7 is pulled out after the coil 9 has been placed into the inside of the aneurysm 1 and the aneurysm 1 has been obturated. This can suppress outflow into the blood vessel 3 of the coil 9 placed in the aneurysm 1 by the stent.

Furthermore, the valving elements 20 of the stent are formed into the mesh pattern with the fractal structure. Furthermore, the insertion portions 11 have no large openings when closed by the respective valving elements 20. Furthermore, the stent has no asperity on the outer periphery thereof and is indwelled in the blood vessel 3 with the outer periphery thereof in contact with the blood vessel wall. As a result, since the stent indwelled in the blood vessel 3 is early covered with cells of the blood vessel wall after the surgery, formation of blood clot can be suppressed in an early stage. Furthermore, since the valving elements 20 are formed into the fractal structure, the closure of the valving element 20 increases the resistance against the flow of blood from the blood vessel 3 into the aneurysm 1 with the result that an amount of blood flowing into the aneurysm 1 can be suppressed.

The present invention should not be limited by the foregoing embodiment described above with reference to the drawings, and the technical scope of the present invention encompasses the following embodiments, for example.

(1) Although the insertion portions are continuously provided on the stent body in the first embodiment, the insertion portions may be provided at intervals on the stent body. In this case, it is better to form the stent body into the mesh pattern, in particular, so that the stent body has the fractal structure.

(2) Four insertion portions are continuously provided in the longitudinal direction (in the circumferential direction in the cylindrical shape) and five insertion portions are continuously provided in the transverse direction (in the axial direction in the cylindrical shape). However, a larger number of insertion portions may be provided, instead.

(3) Although the square insertion portions are formed in the stent body in the first embodiment, the square portions may be formed into another shape. In this case, the valving elements may be formed into a shape according to the insertion portions, instead of the isosceles triangle.

(4) Although each insertion portion is provided with four valving elements in the first embodiment, the number of valving elements may appropriately be changed.

(5) Although the valving elements each have the isosceles triangular shape and are formed into the fractal structure in the first embodiment, the valving elements may be formed into the fractal structure with each having another shape. Furthermore, the valving elements may be formed into a mesh pattern without the fractal structure.

(6) Although the stent body and the valving elements are formed integrally with each other in the first embodiment, the stent body and the valving elements may separately be formed and combined together.

EXPLANATION OF REFERENCE SYMBOLS

1 . . . aneurysm;
7 . . . catheter;
9 . . . coil (embolic material);
10 . . . stent body;
11 . . . insertion portion; and
20 . . . valving element

The invention claimed is:

1. A stent for use in medical treatment of an aneurysm, comprising:
   a stent body having a cylindrical peripheral wall with a plurality of insertion portions through which a catheter is insertable, the insertion portions being arranged side-by-side in both a circumferential direction and an axial direction of the cylindrical peripheral wall; and
   each insertion portion being provided with one or more valving elements that are configured to be opened upon catheter insertion through a respective one of the insertion portions, and to be closed upon catheter pull out from said respective one of the insertion portions, thereby restraining an embolic material placed in the aneurysm from getting out into a blood vessel,
   wherein each insertion portion has a square shape and is provided with four valving elements extending inward from respective sides of the square insertion portion; and
   wherein each valving element has an isosceles triangle shape having an apex located in a central part of the square insertion portion and having three sides one of which corresponds to one of the sides of the square insertion portion.

2. The stent according to claim 1, wherein each valving element has a mesh pattern.

3. The stent according to claim 2, wherein each valving element is made of a material that is identical with a material of the stent body and is formed integrally with the stent body.

4. The stent according to claim 3, which has an outer periphery without any asperity.

5. The stent according to claim 2, which has an outer periphery without any asperity.

6. The stent according to claim 1, wherein each valving element is made of a material that is identical with a material of the stent body and is formed integrally with the stent body.

7. The stent according to claim 1, which has an outer periphery without any asperity.

8. The stent according to claim 1, wherein each valving element has a triangular mesh pattern.

9. The stent according to claim 8, wherein each valving element is made of a material that is identical with a material of the stent body and is formed integrally with the stent body.

10. The stent according to claim 9, which has an outer periphery without any asperity.

11. The stent according to claim 8, which has an outer periphery without any asperity.

12. The stent according to claim 1, wherein each valving element has a mesh pattern of a plurality of types of similar figures differing in size and has a fractal structure.

13. The stent according to claim 12, wherein each valving element is made of a material that is identical with a material of the stent body and is formed integrally with the stent body.

14. The stent according to claim 12, which has an outer periphery without any asperity.

15. The stent according to claim 1 wherein the valving elements are arranged relative to the cylindrical peripheral wall to flex radially outward upon catheter insertion and radially inward upon catheter pull out.

\* \* \* \* \*